United States Patent
Krill et al.

(10) Patent No.: US 9,963,417 B2
(45) Date of Patent: May 8, 2018

(54) PROCESS FOR PRODUCING METHYL METHACRYLATE

(71) Applicants: Steffen Krill, Muehltal (DE);
Alexander Lygin, Griesheim (DE);
Matthias Groemping, Darmstadt (DE);
Torsten Balduf, Pfungstadt (DE);
Rudolf Burghardt, Darmstadt (DE)

(72) Inventors: Steffen Krill, Muehltal (DE);
Alexander Lygin, Griesheim (DE);
Matthias Groemping, Darmstadt (DE);
Torsten Balduf, Pfungstadt (DE);
Rudolf Burghardt, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 5 days.

(21) Appl. No.: 15/037,212

(22) PCT Filed: Dec. 11, 2014

(86) PCT No.: PCT/EP2014/077302
§ 371 (c)(1),
(2) Date: May 17, 2016

(87) PCT Pub. No.: WO2015/091173
PCT Pub. Date: Jun. 25, 2015

(65) Prior Publication Data
US 2016/0280628 A1    Sep. 29, 2016

(30) Foreign Application Priority Data
Dec. 20, 2013  (EP) .................... 13198873

(51) Int. Cl.
C07C 67/39 (2006.01)
B01J 23/89 (2006.01)
C07C 45/75 (2006.01)

(52) U.S. Cl.
CPC ............. *C07C 67/39* (2013.01); *B01J 23/892* (2013.01); *C07C 45/75* (2013.01); *Y02P 20/582* (2015.11)

(58) Field of Classification Search
None
See application file for complete search history.

(56) References Cited

U.S. PATENT DOCUMENTS 6,040,472 A    3/2000  Yamamatsu et al.
RE38,283 E    10/2003  Yamamatsu et al.

OTHER PUBLICATIONS

International Search Report dated Mar. 23, 2015 in PCT/EP2014/077302 filed on Dec. 11, 2014.

(Continued)

*Primary Examiner* — Clinton Brooks
(74) *Attorney, Agent, or Firm* — Oblon, McClelland, Maier & Neustadt, L.L.P.

(57) ABSTRACT

The present invention relates to a catalytic continuous process for producing methyl methacrylate, said process comprising the step of reacting methacrolein with oxygen and methanol in the presence of a heterogeneous noble-metal-containing catalyst in an oxidative esterification reaction to give methyl methacrylate, characterized in that the stationary concentration of the starting material methacrolein is equal to or less than 12% by weight based on the total weight of the reaction mixture in the reactor, and the ratio F between the total liquid volume within the reactor expressed in liters divided by the total weight of catalyst in the reactor expressed in kilograms is equal to or less than 4.

20 Claims, 1 Drawing Sheet

Example of a process flow diagram for the direct oxidative esterification of MAL to MMA according to the present invention

(56) References Cited

OTHER PUBLICATIONS

Written Opinion dated Mar. 23, 2015 in PCT/EP2014/077302 filed on Dec. 11, 2014.
European Search Report dated Apr. 30, 2014 in U.S. Appl. No. 13/198,873, filed Dec. 20, 2013.
U.S. Appl. No. 15/037,171, filed May 17, 2016, Burghardt, et al.

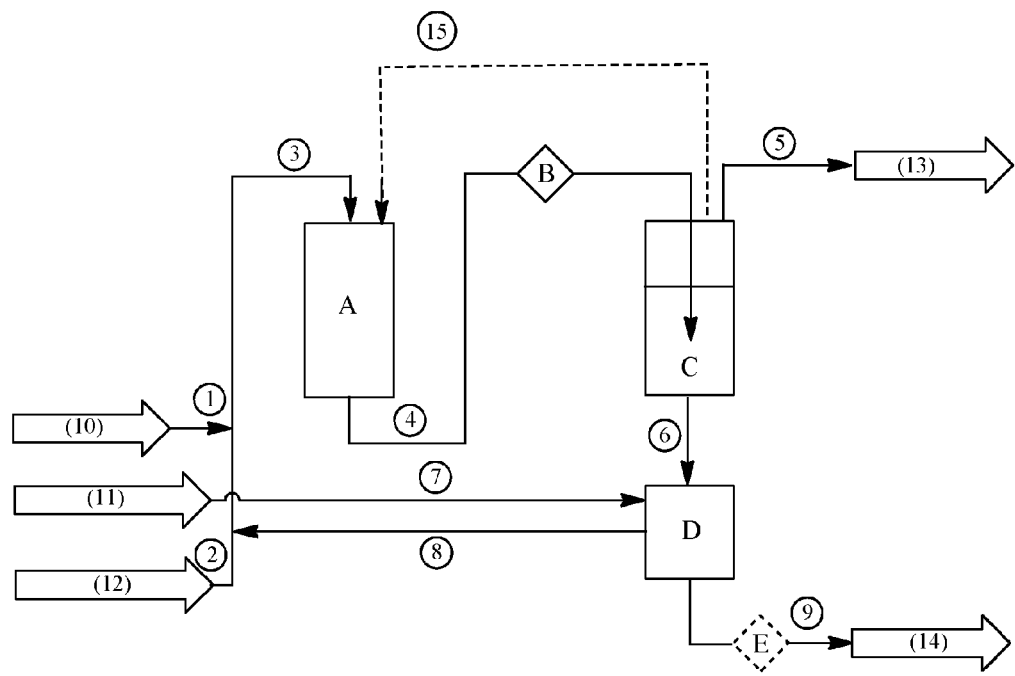
Example of a process flow diagram for the direct oxidative esterification of MAL to MMA according to the present invention

PROCESS FOR PRODUCING METHYL METHACRYLATE

TECHNICAL FIELD OF THE INVENTION

The present invention relates to a process for manufacturing methyl methacrylate by direct oxidative esterification of methacrolein.

BACKGROUND OF THE INVENTION

Large quantities of methyl methacrylate (MMA) are used for producing polymers and copolymers with other polymerizable compounds. The principal application, consuming approximately 80% of the MMA, is the manufacture of polymethyl methacrylate acrylic plastics (PMMA). Methyl methacrylate is also used for the production of co-polymers, such as methyl methacrylate-butadiene-styrene (MBS), used for instance as a modifier for PVC.

It is therefore highly desirable that methyl methacrylate can be produced by a process which results as simple as possible, is cost-effective and protects the environment.

Methyl methacrylate (MMA) is presently manufactured by several industrial methods, the principal one being the acetone cyanohydrin (ACH) route, using acetone and hydrogen cyanide as raw materials by way of the resultant ACH as main intermediate. The intermediate ACH is then converted with sulfuric acid to a sulfate ester of the methacrylamide, methanolysis of which gives ammonium bisulfate and MMA. Although widely used, the ACH route co-produces substantial amounts of ammonium sulfate, treatment of which incurs very high costs.

Other processes, which are not based on the afore-mentioned ACH route, are described in the relevant patent literature and are also well established on a production scale. Among the raw materials used in this context as starting materials are those based on C-4-compounds, for example isobutylene or tert-butanol, which are converted by way of a plurality of stages to the desired methacrylic acid derivatives.

In particular, Asahi Kasei has developed a two-step process for producing MMA, firstly through oxidation of isobutylene or tert-butanol at high temperatures with atmospheric oxygen in the gas phase on a heterogeneous catalyst to give methacrolein (MAL), followed by a second step with oxidative esterification reaction of MAL with methanol and oxygen in the presence of a catalyst. This process is described inter alia in the publications U.S. Pat. No. 5,969, 178 and U.S. Pat. No. 7,012,039. Detailed information about this process is also provided in the article *Trends and Future of Monomer-MMA Technologies, SUMITOMO KAGAKU* 2004-II. In this publication, the direct oxidation process developed by Asahi is described in detail and in particular the disadvantages of the second step corresponding to the direct oxidative esterification step converting MAL to MMA. Indeed, the collection of MAL, recycling of excess methanol, separation of by-products and the like can be assumed to require a large amount of energy. It appears that there is a problem with the yield dropping when trying to raise productivity and reducing the excess methanol to reduce recycling. In general terms, the formation of by-products during the oxidative esterification, such as carbon dioxide, methyl formate, undesired carboxylic ester, requires complicated steps to isolate the final product MMA. For example, the starting material MAL, used in the oxidative esterification, is an extremely unstable compound which is likely to easily undergo a polymerization reaction. These side reactions in the oxidative esterification reactor are strongly to be avoided, because the polymerization of MAL results in clogging and deactivation of the active sites on the catalyst's surface, and causes a decrease in the catalyst's performance. Consequently, it is actually difficult to perform a long-term continuous running because the by-products, such as polymers, tend to accumulate disadvantageously.

This problem is pointed out in JP2004-345974 filed in the name of Asahi Kasei Chemicals Corporation. In said document, it is explained that the small hole of the oxygen diffuser is usually plugged up by polymer by-products, resulting in a bad supply and circulation of oxygen gas in the reactor. The solution proposed in said document is a continuous oxidative esterification process, wherein the temperature of the oxygen in the reactor has to be maintained between 0° C. and 80° C. in order to reduce clogging in the direct oxidative esterification reactor.

Another solution to this clogging problem in the reactor is provided in JP2004-345975, filed in the name of Asahi Kasei Chemicals Corporation. In said document, it is described a continuous oxidative esterification process of MAL to MMA with oxygen and methanol in the presence of a heterogeneous noble-metal-containing catalyst, wherein the polymer by-products are dissolved in methanol and subsequently removed from the reactor.

In U.S. Pat. No. 6,040,472 B1, it is explained that the process from Asahi is only commercially satisfactory when the reaction if performed under special conditions, namely, a reaction temperature as high as 60° C. or more, and a MAL feed concentration of the reaction system as high as 20 wt % or more.

Nevertheless, under these reaction conditions, the selectivity for MMA becomes low and the by-production of methyl formate due to the oxidation of methanol is sharply increased.

As described in U.S. Pat. No. 6,040,472 B1, in order to solve the afore-mentioned problems, Asahi developed a new Pd catalyst to be used in the one-step process for preparing MMA through oxidative esterification of MAL with methanol and oxygen, which allows working under these reaction conditions and still obtain a good yield and selectivity in the direct oxidative esterification of MAL to MMA.

However, there still exists the need to investigate further on possible alternative solutions in order to provide a technically and cost-effective MMA production process with high selectivity, which does not have the disadvantages of the afore-mentioned processes, like for example, by-product formation, too short run time periods for a continuous process because of clogging problems, low MAL conversion and low selectivity in the production of MMA.

DESCRIPTION OF THE INVENTION

Accordingly, the purpose of the present invention is to provide a process for economically producing MMA through a direct oxidative esterification of MAL with methanol and oxygen in the presence of a heterogeneous noble-metal-containing catalyst in a technically feasible manner, with good yield, high selectivity and adequate catalyst activity, while maintaining a relatively low energy usage and a high level of protection of the environment.

After an exhaustive investigation, the inventors have unexpectedly found that by modifying certain reaction parameters, the one-step direct oxidative esterification of MAL to produce MMA could be performed continuously on a large scale with good yield and high selectivity. Under the reaction conditions of the continuous MMA production process as defined in claim 1, MMA can be advantageously produced over long-term continuous campaigns with no clogging problems in the production system, maintaining high MMA selectivity and good reaction activity. The formation of by-products, such as polymers or other condensation products, is reduced, and consequently by-products do not anymore accumulate disadvantageously in the production system and do not anymore interfere with the performance of the catalyst used in the oxidative esterification. This makes the resulting continuous process of the present invention be particularly economically advantageous because it enables preparing MMA with high selectivity over long-term continuous campaigns.

Accordingly, the present invention provides a catalytic continuous process for producing methyl methacrylate comprising the step of reacting MAL with oxygen and methanol in the presence of a heterogeneous noble-metal-containing catalyst in an oxidative esterification reaction, characterized in that
  (a) the stationary concentration of MAL in the reactor of the production process system is equal to or less than 15 wt % of the total weight of the reaction mixture in the reactor, and
  (b) the ratio F, corresponding to the total liquid volume of the reaction mixture within the reactor expressed in liters divided by the total weight of catalyst in the reactor expressed in kilograms, is equal to or less than 4.

Said process as defined in claim 1 not only achieves the above-mentioned objectives, but also advantageously provides a favourable residence time of less than two hours in the reactor by keeping its volume relatively small, which is a very important requirement in large scale processes.

The present process is carried out in a continuous process. Introduction of starting materials into the plant for carrying out a process according to the present invention, and removal of products from the plant, take place here continuously over any desired period of time.

Dependent claims 2 to 14 protect advantageous embodiments of the claimed MMA continuous production process.

Thus, according to other embodiments of the invention, the catalytic continuous process is preferably performed with a stationary concentration of the starting material MAL of less than 12 wt % of the total weight of the reaction mixture in the reactor, even more preferably with a stationary concentration of MAL of less than 8 wt % of the total weight of the reaction mixture in the reactor.

According to other embodiments of the invention, the residence time in reactor is less than 10 h, preferably less than 5 h and even more preferably less than 3 h. The term "residence time" means the average amount of time starting materials are present in the reactor.

The catalytic continuous process may be performed at a temperature of less than 120° C., preferably less than 100° C., and even more preferably between 60 and 90° C.

According to one embodiment of the invention, the oxidative esterification reaction is carried out at a pressure of from 2 to 50 bar.

According to a preferred embodiment of the invention, the reactor used in the claimed process is a fixed-bed reactor.

According to another preferred embodiment of the invention, the reactor used in the process is a fluidized bed reactor.

According to a preferred embodiment of the invention, the oxidative esterification reaction takes place with a molar ratio of methanol to MAL in the range from 1:1 to 50:1.

Preferably, the heterogeneous noble-metal-containing catalyst used in the oxidative esterification reaction comprises one or more ultra-finely dispersed metals with an average particle size of less than 20 nm selected from the group consisting of gold, palladium, ruthenium, rhodium and silver. Especially, the heterogeneous noble-metal-containing catalyst comprises one or more members of the group consisting of lithium, sodium, potassium, calcium, magnesium, scandium, yttrium, lanthanum and other lanthanoids with atomic numbers from 58 to 71, silicon, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, boron, aluminium, gallium, indium, thallium, germanium, tin, lead, antimony, bismuth, tellurium, these being respectively present in metallic and/or oxidized form.

According to a particularly preferred embodiment of the invention, the starting material MAL is prepared by reacting propanal with formaldehyde, optionally provided as aqueous formaldehyde solution, even more preferably in presence of a secondary amine as an organic base and at least one organic acid.

BRIEF DESCRIPTION OF THE DRAWINGS

The present invention can be more easily understood and further advantages are more readily apparent, when considered in view of the detailed description and the following FIGURE in which:

FIG. 1 illustrates, by way of example, a process flow diagram for the direct oxidative esterification of MAL to MMA according to the present invention.

KEY

FIG. 1
(A) Reactor
(B) Heat exchanger
(C) Gas/liquid separator
(D) Neutralization vessel, where the pH is adjusted to pH=5 to 9
(E) Alternative or additional heat exchanger
(1) Supply line for the gas phase comprising oxygen (11)
(2) Supply line for liquid reactants (methanol and MAL) (13)
(3) Supply line for mixing gas phase (11) with liquid reactants (13)
(4) Line from reactor (A) to gas/liquid separator (C) and heat exchanger (B)
(5) Output line for off-gas (14) from gas/liquid separator (C)
(6) Line from gas/liquid separator (C) to neutralization vessel (D)
(7) Supply Line for basic solution (12) into neutralization vessel (D)
(8) Recycling line for sending back a part of the reaction mixture with adjusted pH to the reactor (A) via line (3) under mixing with gas phase (11), which is supplied via line (1)
(9) Output line for the MMA containing liquid phase (15) for purification
(10) Gas phase comprising oxygen
(11) Basic solution
(12) Liquid reactants (methanol and MAL)
(13) Off-gas
(14) MMA containing liquid phase
(15) Recycling line for sending part of the oxygen-containing gas back to the oxygen-containing gas supply

EXEMPLARY IMPLEMENTATION OF THE INVENTION

As indicated above, one possible implementation of the described invention is shown in FIG. 1. In the process oxygen or gas containing oxygen (preferably a mixture with an inert component, e.g. $N_2$) is fed over line 1, while the MAL/methanol mixture is fed over line 2 into reactor A. These components are mixed and the resulting heterogeneous gas/liquid mixture is fed over line 3 to a fixed bed reactor A with an external heat exchanger, thereby the gas/liquid mixture as well as the individual components thereof can be fed from the upper as well as from the lower part of the reactor.

The reactor is filled with a corresponding fixed bed catalyst with an average diameter of more than 200 µm. Here, this particle size was necessary to prevent a pressure build-up inside the reactor. On the other hand, the particle size is limited to a maximum of 20 mm to optimize the area of contact between the catalyst and the reactants. Catalysts with a core-shell distribution of the active component on a support core are preferably used.

The mixture is fed after the reaction over line 4 from reactor A into the heat exchanger B, where it is cooled. After cooling, the mixture is fed into a gas/liquid separator C, where the gas phase is continuously separated from the liquid phase (preferentially at lower temperature and higher pressure).

The off-gas can be disposed of over line 5 or preferably recycled over line 16.

The liquid phase is optionally fed over line 6 to a neutralization vessel D, where the pH is adjusted to be between 5 and 9 by adding a basic solution (e.g. NaOH in MeOH).

The reaction mixture comprising MMA is separated from this neutralization vessel D over the output line 9 for further purification, while the rest of the reaction mixture is fed back to reactor A over line 8.

In an especially preferred embodiment of the invention the mixture is not cooled in the heat exchanger B (B is not applied here). Thereby the recycled fraction is fed into the reactor A at reaction temperature, while the diverted fraction for purification is fed into the heat exchanger E where it is cooled.

In further embodiments of the invention other reactors then fixed bed reactors may be used. As subject to the reactor technology the catalyst may vary in the particle size. In the case of a slurry-bed reactor, for instance, a powder catalyst with a particle size of less than 0.2 mm is preferred.

Any conventional reactors can be chosen for performing the oxidative esterification according to the invention. Reactors suitable for the claimed production process are, by way of example, a stirred tank reactor or a bubble column with suspended catalyst. These reactors offer a close approach to isothermal operating conditions. According to the invention, it is advantageous to use a catalytic fixed-bed reactor in the claimed production process because these reactors are suited to high-pressure processes by virtue of their simple design. Fixed-bed reactors also enable operating continuous catalytic processes with a favourable utilization of the catalyst volume without attrition and losing of catalysts. A fluidized bed reactor is another possible reactor form which can be applied.

Typical reactor volumes for a continuously operated production plant can be, by way of example, a tubular/tube-bundle reactor of capacity from 10 to 15 $m^3$ or a continuously operated stirred tank of capacity from 50 to 100 $m^3$, but these data are not intended to represent any restriction.

As indicated above, the heterogeneous noble-metal-containing catalyst used in the oxidative esterification reaction according to the invention comprises one or more ultrafinely dispersed metals with an average particle size of less than 20 nm selected from the group consisting of gold, palladium, ruthenium, rhodium and silver. Particularly preferred is gold as catalytically active component. The catalysts with a core-shell distribution of the active component on support are preferably used.

The average diameter of catalyst for direct oxidative esterification of MAL to methyl methacrylate mostly suitable for application in a stirred tank or a bubble column/fluidized bed reactor with suspended catalyst is 200 µm or less.

The average diameter of catalyst for direct oxidative esterification of MAL to methyl methacrylate mostly suitable for application in a fixed bed reactor is more than 200 µm.

EXAMPLES

The invention is illustrated further in the following non-limiting examples 1 to 3 and comparative examples 1 and 2. The examples 1 to 3 below serve for further explanation of preferred embodiments according to the present invention, but are not intended to restrict the invention. All results are shown in Table 1.

Example 1: Preparation of Catalyst 1 (0.9% Au-1.1% NiO on $SiO_2$—MgO)

A solution of 51.2 g of magnesium nitrate hexahydrate and 5.4 g of 60% nitric acid in 100 mL of water was added at 20° C. to 108 g of $SiO_2$ carrier (Fuji Silicia, Cariact Q-10, 0.85-1.75 mm). The mixture was stirred at 50° C. for 24 hours, then cooled to room temperature, dried and calcined. 30 g of this $SiO_2$—MgO support were suspended in 100 mL of water and heated to 90° C. After 15 min at 90° C., a solution of 1.64 g of nickel nitrate hexahydrate and 530 mg of auric acid ($HAuCl_4$) in 100 mL of water was added dropwise during 30 min to this suspension. After stirring at 90° C. for further 30 minutes, the mixture was cooled and the solid was removed, then washed three times with 100 mL of fresh water and in each case stirred at 20° C. for 5 minutes and filtered off. The catalyst was dried at 105° C. over a period of 10 hours and calcined at 450° C. over a period of 5 hours. ICP analysis (inductively coupled plasma mass spectrometry) showed that the resultant violet powder comprised 1.1% of Ni and 0.9% of Au. The average size of gold nanoparticles (TEM) was less than 5 nm.

Example 2: Preparation of MMA Via Direct Oxidative Esterification of MAL

A mixture of 30.9 wt % of MAL and 69.1 wt % of methanol was brought to pH=7 by addition of a 1% sodium hydroxide solution in methanol. This neutralized mixture was then fed at a flow rate of 20.9 g/h along with $O_2/N_2$ gas mixture (7 vol % $O_2$) at 6 bar to a tube reactor with outer heat exchanger (80° C.). The residual $O_2$ content in off-gas was adjusted to 4 vol %. The reactor contained 15 g of catalyst 1. By continuous addition of a 1% sodium hydroxide solution in methanol to the neutralization vessel, the pH was maintained at pH 7 in the system. The ratio of over line 12 recycled mixture and product output 11 was R/P=10. The product mixture was analyzed by gas chromatography. Table 1 shows the results obtained after 73 h having the MMA production process running, as well as after 512 h.

Example 3: Preparation of MMA Via Direct Oxidative Esterification of MAL with Lower Feed Rate and Lower MAL Concentration Within the Feed Example 3 was carried out under the same operating conditions as Example 2, but with a feed flow rate of 15.1 g/h, and a feed concentration of 45.3 wt % of MAL and 54.7 wt % of methanol.

Comparative Example 1: Preparation of MMA Via Direct Oxidative Esterification of MAL with a MAL Stationary Concentration Higher than 15 wt % in the Reactor Comparative Example 1 was carried out under the same operating conditions as Example 2, but with a feed flow rate of 10.3 g/h, and a feed concentration of 63 wt % of MAL and 27 wt % of methanol. The MAL stationary concentration in the reactor was higher than 15 wt %.

Comparative Example 2: Preparation of MMA Via Direct Oxidative Esterification of MAL with a MAL Stationary Concentration Higher than 15 wt % and with a Ratio F Higher than 4

Comparative Example 2 was carried out under the same operating conditions as Example 2, but with a feed flow rate of 21 g/h, 5 g of catalyst 1, and a feed concentration of 33.3 wt % of MAL and 66.7 wt % of methanol. The MAL stationary concentration was higher than 15 wt % and the ratio F as defined above was higher than 4.

As shown in Table 1, very good results over long times on stream are obtained when the production of MMA is carried out using the specific reaction parameters as claimed in the present invention, namely a MAL stationary concentration in the reactor of less than 15 wt % combined with a ratio F as defined in claim 1 of less than 4 (see Examples 2 and 3).

Indeed, as shown in Example 2, at 73 hours after the start of the production, the MAL conversion rate was 70.8% and the selectivity rate of MMA was 97.4%. At 512 h after the start of the production, the MAL conversion rate was 69.8% and the selectivity rate of MMA was 97.2%, thus showing hardly any change in reactivity. The process was still running with no problem of line clogging (no formation of polymer by-products), and the MMA selectivity was still very high.

On the contrary, Comparative Examples 1 and 2 show a decrease in reaction activity and MMA selectivity when at least one of the reaction parameters (namely, ratio F and/or MAL stationary concentration) is not complying with the claimed combination of reaction parameters as defined in claim 1 of the present invention.

As shown in Comparative Example 1, when the ratio F is less than 4 (F=1.7), but the MAL stationary concentration is more than 15 wt %, namely 20.2 wt % at a time on stream of 71 h, or 32.1 wt % at time on stream of 173 h, then the MMA selectivity is only 82.5% or 68.7%, respectively. The conversion rate of MAL has also drastically decreased with 45.1% at a time on stream of 71 h, and only 27.8% at a time on stream of 173 h, thus showing decreases in reaction activity and selectivity.

In Comparative Example 2, even if the space time yield is good with an average of 6.1 mol MMA/kg cat h, the MMA selectivity is low with only 83.5% after 71 h and even a lower selectivity after 236 h with only 79.6%. In a continuous production process, the space time yield is not so important, because the reaction mixture is always recycled back to the reactor and thus, the key factor is the overall yield. Therefore, high selectivity is required in order to get a high overall yield, which is crucial to make the process be effective and economically advantageous.

On the basis of the above results, it is clearly demonstrated that both reaction parameters, namely a MAL stationary concentration in the reactor of less than 15 wt % and a ratio F of less than 4 as claimed in the present invention, are needed in order to produce MMA over long-term continuous campaigns with no clogging problems in the production system, maintaining high MMA selectivity and good reaction activity. In addition, under these reaction conditions, the formation of by-products is reduced, thus improving the performance of the catalyst used in the oxidative esterification.

Although illustrated and described herein with reference to certain specific embodiments, the present invention is nevertheless not intended to be limited to the details shown. Rather, various modifications may be made in the details within the scope of the claims.

The invention claimed is:

1. A catalytic continuous process for producing methyl methacrylate comprising reacting methacrolein with oxygen and methanol in the presence of a heterogeneous noble-metal-containing catalyst in an oxidative esterification reaction in a reactor, wherein
   (a) a stationary concentration of methacrolein is equal to or less than 15% by weight based on the total weight of the reaction mixture in the reactor, and
   (b) a ratio F, between the total liquid volume within the reactor expressed in liters divided by the total weight of catalyst in the reactor expressed in kilograms, is equal to or less than 4 L/kg.

TABLE 1

| No. | Time on stream [h] | Conversion MAL [%] | MAL conc. feed [wt %] | MAL conc. in reactor [wt %] | Feed [g/h] | Residence time in reactor [h] | F [mL/g] | Space Time Yield [mol MMA/ kg cat h] | Selectivity MMA [%] |
|---|---|---|---|---|---|---|---|---|---|
| Example 2 | 73 | 70.8 | 30.9 | 6.58 | 20.9 | 1 | 1.7 | 4.12 | 97.4 |
|  | 512 | 69.8 | 30.9 | 6.75 | 20.9 | 1 | 1.7 | 4.06 | 97.2 |
| Example 3 | 48 | 65.1 | 45.3 | 9.76 | 15.1 | 1.3 | 1.7 | 3.84 | 91.3 |
|  | 311 | 54.3 | 45.3 | 13.2 | 15.1 | 1.3 | 1.7 | 3.16 | 90.2 |
| Comp. Ex. 1 | 71 | 45.1 | 63 | 20.2 | 10.3 | 2 | 1.7 | 2.25 | 82.5 |
|  | 173 | 27.8 | 63 | 32.1 | 10.3 | 2 | 1.7 | 1.20 | 68.7 |
| Comp. Ex. 2 | 71 | 36.8 | 33.3 | 18.66 | 21.0 | 1 | 5 | 6.14 | 83.5 |
|  | 236 | 37.2 | 34.5 | 19.60 | 21.0 | 1 | 5 | 6.16 | 79.6 |

2. The catalytic continuous process according to claim 1, wherein the stationary concentration of methacrolein is less than 12% by weight based on the total weight of the reaction mixture in the reactor.

3. The catalytic continuous process according to claim 2, wherein the stationary concentration of methacrolein is less than 8% by weight based on the total weight of the reaction mixture in the reactor.

4. The catalytic continuous process according to claim 1, wherein a residence time in the reactor is less than 10 h.

5. The catalytic continuous process according to claim 4, wherein the residence time in the reactor is less than 3 h.

6. The catalytic continuous process according to claim 1, wherein the oxidative esterification is carried out at a temperature in the reactor of less than 120° C.

7. The catalytic continuous process according to claim 1, wherein the oxidative esterification reaction is carried out at a pressure of from 2 to 50 bar.

8. The catalytic continuous process according to claim 1, wherein the reactor is a fixed-bed reactor.

9. The catalytic continuous process according to claim 8, wherein the heterogeneous noble-metal-containing catalyst used for the oxidative esterification reaction has an average diameter of more than 200 µm.

10. The catalytic continuous process according to claim 1, wherein the reactor is a fluidized bed reactor.

11. The catalytic continuous process according to claim 10, wherein the heterogeneous noble-metal-containing catalyst used for the oxidative esterification reaction has an average diameter of 200 µm or less.

12. The catalytic continuous process according to claim 1, wherein the oxidative esterification reaction takes place with a molar ratio of methanol to methacrolein in the range from 1:1 to 50:1.

13. The catalytic continuous process according to claim 1, wherein the heterogeneous noble-metal-containing catalyst used for the oxidative esterification reaction comprises at least one ultra-finely dispersed metal with an average particle size of less than 20 nm selected from the group consisting of gold, palladium, ruthenium, rhodium and silver.

14. The catalytic continuous process according to claim 13, wherein the heterogeneous noble-metal-containing catalyst used for the oxidative esterification reaction comprises at least one member selected from the group consisting of lithium, sodium, potassium, calcium, magnesium, scandium, yttrium, lanthanum and other lanthanoids with atomic numbers from 58 to 71, silicon, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, boron, aluminium, gallium, indium, thallium, germanium, tin, lead, antimony, bismuth, and tellurium, these being respectively present in metallic and/or oxidized form.

15. The catalytic continuous process according to claim 1, wherein methacrolein is prepared by reacting propanal with formaldehyde in a Mannich condensation reaction in presence of a secondary amine as an organic base and at least one organic acid.

16. The catalytic continuous process according to claim 1, wherein the oxidative esterification is carried out at a temperature in the reactor of between 60 and 90° C.

17. The catalytic continuous process according to claim 1, wherein the heterogeneous noble-metal-containing catalyst used for the oxidative esterification reaction comprises at least one ultra-finely dispersed metal with an average particle size of less than 20 nm selected from the group consisting of gold, ruthenium, rhodium and silver.

18. The catalytic continuous process according to claim 1, wherein the heterogeneous noble-metal-containing catalyst comprises gold and nickel.

19. The catalytic continuous process according to claim 1, wherein the heterogeneous noble-metal-containing catalyst comprises a $SiO_2$—MgO support.

20. The catalytic continuous process according to claim 1, wherein the heterogeneous noble-metal-containing catalyst comprises ultra-finely dispersed gold with an average particle size of less than 5 nm.

* * * * *